US012545448B2

(12) United States Patent
Boira Bonhora et al.

(10) Patent No.: US 12,545,448 B2
(45) Date of Patent: Feb. 10, 2026

(54) METHOD OF DOSING STERILE SYRINGES AND DEVICE FOR USE WITH SAID METHOD

(71) Applicant: GRIFOLS ENGINEERING, S.A., Parets del Valles (ES)

(72) Inventors: Jordi Boira Bonhora, Parets del Valles (ES); Manuel Garcia Sanchez, Parets del Valles (ES)

(73) Assignee: GRIFOLS ENGINEERING, S.A., Parets del Valles (ES)

( * ) Notice: Subject to any disclaimer, the term of this patent is extended or adjusted under 35 U.S.C. 154(b) by 57 days.

(21) Appl. No.: 18/579,655

(22) PCT Filed: Jul. 18, 2022

(86) PCT No.: PCT/ES2022/070465
§ 371 (c)(1),
(2) Date: Jan. 16, 2024

(87) PCT Pub. No.: WO2023/002078
PCT Pub. Date: Jan. 26, 2023

(65) Prior Publication Data
US 2024/0343428 A1 Oct. 17, 2024

(30) Foreign Application Priority Data
Jul. 19, 2021 (EP) .................................... 21382654

(51) Int. Cl.
*B65B 3/00* (2006.01)
*A61M 5/00* (2006.01)
*B65B 55/06* (2006.01)

(52) U.S. Cl.
CPC ............ *B65B 3/003* (2013.01); *A61M 5/008* (2013.01); *B65B 55/06* (2013.01)

(58) Field of Classification Search
CPC ........ B65B 55/06; B65B 3/003; A61M 5/008; A61M 2207/00
See application file for complete search history.

(56) References Cited

U.S. PATENT DOCUMENTS

| | | | | |
|---|---|---|---|---|
| 4,729,208 A * | 3/1988 | Galy | A61M 5/00 | 53/328 |
| 2004/0139698 A1* | 7/2004 | Grifols Lucas | B65B 3/003 | 53/426 |

(Continued)

FOREIGN PATENT DOCUMENTS

FR 3 062 065 A1 7/2018

OTHER PUBLICATIONS

International Search Report for PCT/ES2022/070465 Issued Sep. 23, 2022, which is related to the present application.

*Primary Examiner* — Himchan Song
(74) *Attorney, Agent, or Firm* — Knobbe, Martens, Olson & Bear LLP

(57) ABSTRACT

A method for dosing sterile syringes with medicinal products includes arranging syringes in a syringe nest and the syringe nest in a device with a cover, sterilizing the syringes, loading the devices with the syringes in a dispensing system, and uncovering, dosing and covering the syringes by a dosing system in the presence of a laminar flow. The device allows the nests to be sterilized and the cover protects the inside of the syringes from suspended particulates.

12 Claims, 9 Drawing Sheets

(56) References Cited

U.S. PATENT DOCUMENTS

| | | | | |
|---|---|---|---|---|
| 2008/0087353 | A1* | 4/2008 | Py | B65B 57/00 141/130 |
| 2012/0090268 | A1* | 4/2012 | Krauss | B65B 3/003 53/281 |
| 2013/0161225 | A1* | 6/2013 | Lepot | B01L 9/54 206/557 |
| 2018/0072446 | A1* | 3/2018 | Naing | B65B 55/027 |
| 2024/0343428 | A1* | 10/2024 | Boira Bonhora | B65B 55/06 |

* cited by examiner

METHOD OF DOSING STERILE SYRINGES AND DEVICE FOR USE WITH SAID METHOD

PRIORITY AND CROSS REFERENCE TO RELATED APPLICATIONS

This application is the U.S. National Phase Application under 35 U.S.C. § 371 of International Application No. PCT/ES2022/070465, filed Jul. 18, 2022, designating the U.S. and published as WO 2023/002078 A1 on Jan. 26, 2023, which claims the benefit of European Application No. 21382654.8, filed Jul. 19, 2021. Any and all applications for which a foreign or a domestic priority is claimed is/are identified in the Application Data Sheet filed herewith and is/are hereby incorporated by reference in their entireties under 37 C.F.R. § 1.57.

FIELD OF INVENTION

The present invention relates to a novel method for dosing sterile syringes and to a device for use with said method, which confers significant advantages compared with that known in the present state of the art.

In particular, the present invention relates to a method for dosing sterile syringes that can be applied to medicinal products which provides a guarantee of sterility when dosing. More specifically, the present invention applies to a novel method of reducing exposure of the inside of the syringes to particulate pollutants and thus ensuring sterile dosing of the syringes.

BACKGROUND

Automated syringe dosing methods and systems with a wide variety of characteristics are known in the prior art. Dosing systems exist in the prior art which comprise a dosing area in which said dosing is carried out using a robotic arm which handles a number of dispensing units. Said dosing systems dose the syringes either individually or in a group under sterile conditions and usually while subjecting said syringes to a vertical laminar flow. This means that the laminar airflow coming from the area above the system is partly impeded by the dispensing system, causing turbulence in the flow that reaches the syringes and significantly reducing the protection said flow would provide under laminar conditions. Moreover, said dosing systems do not usually envisage protecting the open end of the syringes by a physical barrier, which results in a risk of contamination by suspended particulates.

Furthermore, syringe dosing methods and the corresponding systems wherein dosing is carried out individually are known in the prior art.

SUMMARY

In a first aspect, the present invention relates to a method for dosing sterile syringes with medicinal products which includes: (a) arranging a group of syringes in a syringe nest and the syringe nest in turn in a device, the device comprising a cover; (b) sterilizing the syringes thus arranged, the sterilization being performed by a thermal process; (c) loading the devices with the sterile syringes in a dispensing system in order to dose the syringes; (d) uncovering, dosing and covering the syringes using a dosing system in the presence of a laminar flow, where the device allows sterilization of the nests and protects the inside of the syringes from suspended particulates by means of the cover, which acts as a physical barrier. In some embodiments, the sterilization is carried out in an autoclave with steam. In some embodiments, cooling step is carried out in a sterile area of the autoclave. In some embodiments, the syringes are uncovered by removing the cover from the device.

In some embodiments, the uncovering, dosing and covering step is carried out in a dosing area which is in the presence of a laminar flow, where the laminar flow is a horizontal laminar flow, the devices being arranged in such a way that a base of the device is parallel to the horizontal laminar flow, so that the longitudinal axis of the syringes is substantially vertical and the open end thereof is facing upwards.

In some embodiments, the uncovering, dosing and covering step is carried out under class II, type A conditions (DIN EN 12469:2000-09).

In some embodiments, a device for dosing sterile syringes according to the method described above includes: a substantially prism-shaped structure in which at least an upper face is an open face which defines a perimeter area relative to the open face, the perimeter area having a vertical peripheral surface, the structure also comprising lateral surfaces with upper ends close to the open upper face and lower ends close to a base, the structure being arranged so as to allow the syringe nests to be inserted through at least said open upper face and a cover which, in the closed position, rests on the perimeter area of the open upper face of the device, the cover being arranged so as to cover the syringes.

In some embodiments, a device for receiving syringe nests in order to carry out the method for dosing sterile syringes described above includes a substantially prism-shaped structure in which at least an upper face is an open face which defines a perimeter area relative to the open face, a vertical peripheral surface being arranged on the perimeter area, the structure also include lateral surfaces with upper ends close to the open upper face and lower ends close to a base, the structure being arranged so as to allow the syringe nests to be inserted through at least said open upper face and a cover which, in the closed position, rests on the perimeter area of the open upper face of the device, the cover being arranged so as to cover the syringes. In some embodiments, the device further includes an edge on the perimeter area of the open upper face on which a peripheral portion of the syringe nest rests and support surfaces arranged between the lateral surfaces, so that said inner edge and said support surfaces distribute the load applied by the syringes to the device, thus reducing the stresses to which the syringe nest is subjected.

In some embodiments, the cover of the device includes protrusions which project towards the inside of the device, encircling the open ends of the syringes. In some embodiments, the cover of the device includes a skirt arranged around the perimeter thereof, encircling the device and contacting the vertical peripheral surface of the device by means of a peripheral protrusion.

In some embodiments, the cover of the device comprises fastening means to act on the device. In some embodiments, the fastening means are dimensional interference fastening means. In some embodiments, the structure of the device includes reception means for receiving the means for fastening the cover.

BRIEF DESCRIPTION OF THE DRAWINGS

These and other advantages and characteristics of the invention will be made clear in view of the figures and the detailed description of the invention. Said figures should be understood as an explanatory but non-limiting example of an embodiment of the dosing system according to the present invention.

DETAILED DESCRIPTION

Figure 1:
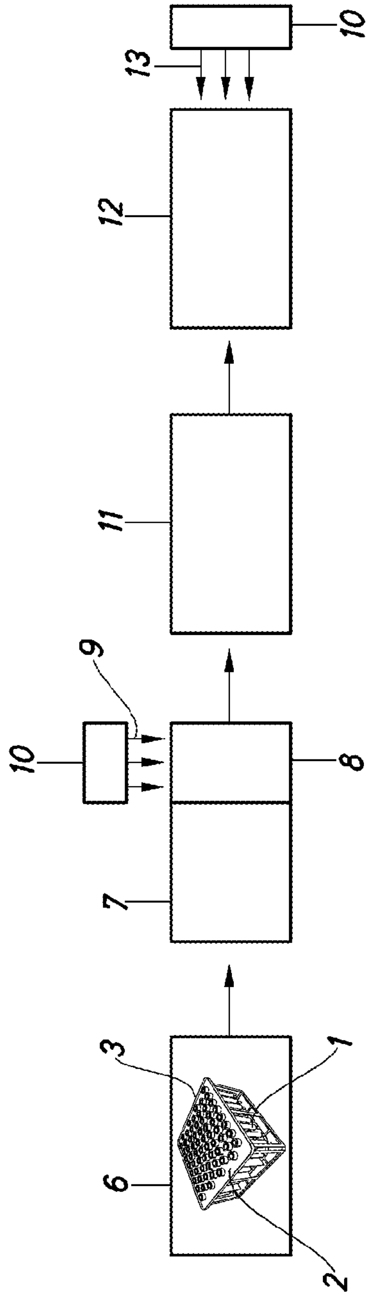
FIG. 1 is a diagram of the steps of the syringe dosing method according to the present invention.

An object of the present invention is to disclose a dosing method and a device for carrying out said method which allows the entire syringe dosing method to be carried out safely, from sterilisation in an autoclave to dosing and covering the syringes, limiting the time the syringes are exposed to suspended particulates, said method also being effective.

To attain this object, a method for dosing sterile syringes with medicinal products is used which comprises the following steps:

a) Arranging a group of syringes in a syringe nest and said syringe nest in turn in a device, said device comprising a cover;

b) sterilising the syringes thus arranged, said sterilisation being performed by a thermal process;

c) loading the devices with the sterile syringes in a dispensing system in order to dose the syringes;

d) uncovering, dosing and covering the syringes using a dosing system in the presence of a laminar flow, while keeping said syringes sterile;

wherein said device allows sterilisation of the syringes and protects the inside of the syringes from suspended particulates by means of the cover, which acts as a physical barrier.

The device according to the present invention allows sterilisation to take place without the syringe nests suffering significant deformations, preferably by providing said syringe nests with a support, and at the same time preferably has means for protecting the interior of the syringes.

Preferably, the thermal process may be sterilisation with steam in an autoclave. Other thermal processes are also possible, such as sterilisation by delivering air or another gas with controlled temperature properties.

Preferably, the syringes are sterilised in an autoclave with saturated steam.

Preferably, the syringe cooling step is carried out in a sterile area of the autoclave where the presence of a laminar flow is not necessary. This cooling step may be carried out by supplying clean process air/filtered air, the flow and/or temperature of which can be controlled over time. This process is usually referred to as "tempering". If desired, the density and/or pressure conditions may also be controlled to minimise the risk of air entering, this step being carried out in an area of maximum environmental control and quality.

More preferably, the syringes are uncapped by removing the cover from the device. This allows the syringe dosing method to be much more efficient than alternatives such as uncovering the syringes individually.

More preferably, the syringes are capped individually after being dosed.

Still more preferably, the syringe dosing method also has a step of weighing at least one of the dosed syringes. Said weighing step allows the calibration of the dosing system to be checked.

Still more preferably, the step of loading the devices in the dispensing system is performed automatically using automatic distribution means such as robotic arms and/or conveyor belts. However, the loading step may also be carried out manually by qualified technicians or semi-automatically.

Advantageously, the syringe uncovering, dosing and covering step is carried out in a dosing area which is subjected to a horizontal laminar flow, the devices being arranged with a base thereof parallel to the horizontal laminar flow so that the longitudinal axis of the syringes is substantially vertical and the open end thereof is facing upwards.

More advantageously, the syringe uncovering, dosing and covering step is carried out in an environment under class II, type A conditions (DIN EN 12469:2000-09). These conditions protect the operators in the vicinity from the products being handled, and the medicinal products from contamination by the external environment.

Still more advantageously, during the syringe dosing, the device is arranged so that the horizontal laminar flow is not impeded or obstructed at least until reaching an open end of the syringes. This is particularly advantageous when the syringes are subject to a horizontal laminar flow, as the laminar flow can be maintained, significantly reducing the presence of turbulence in the vicinity of the open ends of the syringes.

In addition, preferably, the device for the method described above comprises:

a substantially prism-shaped structure in which at least an upper face is an open face which defines a perimeter area relative to the open face, said structure comprising lateral surfaces with upper ends close to the open upper face and lower ends close to a base, said structure being arranged so as to allow the syringe nests to be inserted through at least said open upper face;

a cover which in the closed position rests on a perimeter of the open upper face of the device, said cover being arranged so as to cover the syringes.

In addition, the present invention also discloses a device for receiving syringe nests which comprises:

a substantially prism-shaped structure in which at least an upper face is an open face which defines a perimeter area relative to the open face, a vertical peripheral surface being arranged on said perimeter area, said structure also comprising lateral surfaces with upper ends close to the open upper face and lower ends close to a base, said structure being arranged so as to allow the syringe nests to be inserted through at least said open upper face;

a cover which, in the closed position, rests on the perimeter area of the open upper face of the device, said cover being arranged so as to cover the syringes.

The inside of the structure of the device may also communicate with the outside through the lateral surfaces and/or base thereof, so that steam from the autoclave can access the syringe nests arranged in the device at multiple points from the outside via said open surfaces. In addition, the cover is a physical barrier and significantly reduces the risk of suspended particulates penetrating the interior of the syringes.

Preferably, the device also comprises an edge on the perimeter area of the open upper face on which a peripheral portion of the syringe nest rests and syringe nest support surfaces arranged between the lateral surfaces of the device.

Both the edge and the support surfaces act as contact areas between the syringe nest and the device and distribute the load applied by the syringes to the device, thus reducing the stresses to which the syringe nest is subjected.

More preferably, the cover of the device is independent of the device, in other words, the cover and the device are not mechanically connected.

Still more preferably, the cover of the device comprises protrusions which project towards the inside of the device, encircling the open ends of the syringes. Equally preferably, the cover of the device comprises a skirt arranged around the perimeter thereof, encircling the device around the perimeter thereof and in turn contacting a vertical surface arranged on the perimeter area of the open upper face by means of a peripheral protrusion. Advantageously, the cover may comprise fastening means to act on the device, said fastening means being advantageously dimensional interference means. However, the fastening means may also comprise magnetic and/or resilient elements to facilitate the closing or opening of the cover.

Said cover arrangements on the devices create labyrinthine communication between the outside and the inside of the syringes, which is particularly advantageous when protecting the inside of the syringes from suspended particulates.

Said reception means may comprise indentations, tapers, shaped profiles or other reception means known in the prior art.

Preferably, the device is made of a material that is resistant both to high temperatures (up to at least 150° C.) and high temperature gradients. Said material may be stainless steel, metal alloys or other known materials.

The use of said devices facilitates handling of the syringe nests given that said syringe nests, on being subjected to high temperatures during the sterilisation step, tend to deform owing to the weight of the syringes. However, when syringe nests are arranged in the devices according to the present invention, the syringe nests transfer the load or weight of the syringes to said devices, thus preventing deformation of the syringe nests. This is particularly advantageous when carrying out the subsequent steps of the method, since preventing deformation of the syringe nests facilitates the dosing thereof. Indeed, any severe deformations the syringe nest might suffer would in particular make it significantly difficult to handle said syringe nest, which would in turn affect the correct distribution and alignment of the syringes, possibly making dosing of the syringes impossible.

Preferably, in the method for dosing sterile syringes according to the present invention, the device is a device as described above.

The term "dosing" refers to partly or completely filling the syringe with a predetermined amount. The term "syringe nest" refers to a physical support in which a group of syringes may be arranged individually. The terms "lower", "upper" and "lateral" refer to a relative arrangement between the components on which they are associated; said terms should not be understood as a limitation with regard to the arrangement of said components with respect to the general orientation of the dosing system. The terms "horizontal" and "vertical" refer to an arrangement substantially parallel to the ground and parallel to the direction of gravitational attraction, respectively, said orientations being substantially perpendicular.

A syringe dosing method according to the present invention will be described in detail below.

The sterile syringe dosing method of FIG. 1 begins with the step 6 of arranging the syringes 1 in the syringe nests 2, and said syringe nests in turn in the device 3. Next, the unit made up of the syringes 1, the syringe nests 2 and the devices 3 undergoes sterilisation 7 in an autoclave. The cover of the device 3 has not been shown for reasons of clarity. Said unit is introduced into the autoclave, sterilisation 7 being carried out with steam, preferably saturated steam. Furthermore, one or more units made up of syringes 1, syringe nests 2 and devices 3 may be arranged on trays and/or trolleys to facilitate handling of said units when being introduced and removed from the autoclave.

Next, said units made up of the syringes 1, the syringe nests 2 and the devices 3, and more specifically the syringes 1, are subjected to cooling 8. Said cooling is preferably carried out in the autoclave. Optionally, this step may take place in a filtered laminar airflow 9 of class II, type A (DIN EN 12469:2000-09), produced by known ventilation means 10, minimising the risk of air entering when the syringes are cooled by a reduction in air density, said filtered laminar airflow 9 forming a basically one-directional refrigeration circuit from entry to the apparatus 10 to exit from the sterile area of the autoclave.

The next step in the method relates to the delivery 11 of the units made up of the syringes 1, the syringe nests 2 and the devices 3 to a dosing system. Said delivery 11 may be carried out automatically using known delivery means such as robotic arms or conveyor belts, among others. Moreover, delivery 11 may be effected with the supervision and/or collaboration of qualified technical staff, semi-automatically or manually.

Next, the syringe uncovering, dosing and covering step 12 is carried out in a dosing area where the devices 3 are uncovered to allow the dosing system to access the syringes 1 and carry out the dosing 12. Once dosing is complete, the syringes are capped. These operations are carried out in a dosing area under a filtered laminar airflow, preferably under class II, type A conditions (DIN EN 12469:2000-09), and subjected to a horizontal laminar flow 13 produced by known ventilation means 10. Moreover, as explained above, the arrangement of the devices 3 relative to said horizontal laminar flow 13 is such as to ensure the horizontal laminar flow 13 does not encounter any obstacle or obstruction before reaching the open end of the syringes 1. This arrangement prevents turbulence from being produced in the vicinity of the open ends of the syringes 1, reducing the possibility of suspended particulates contaminating said syringes.

In addition, during or after dosing, one or more dosed syringes may be weighed to check that the dosing system is correctly calibrated.

Figure 2:
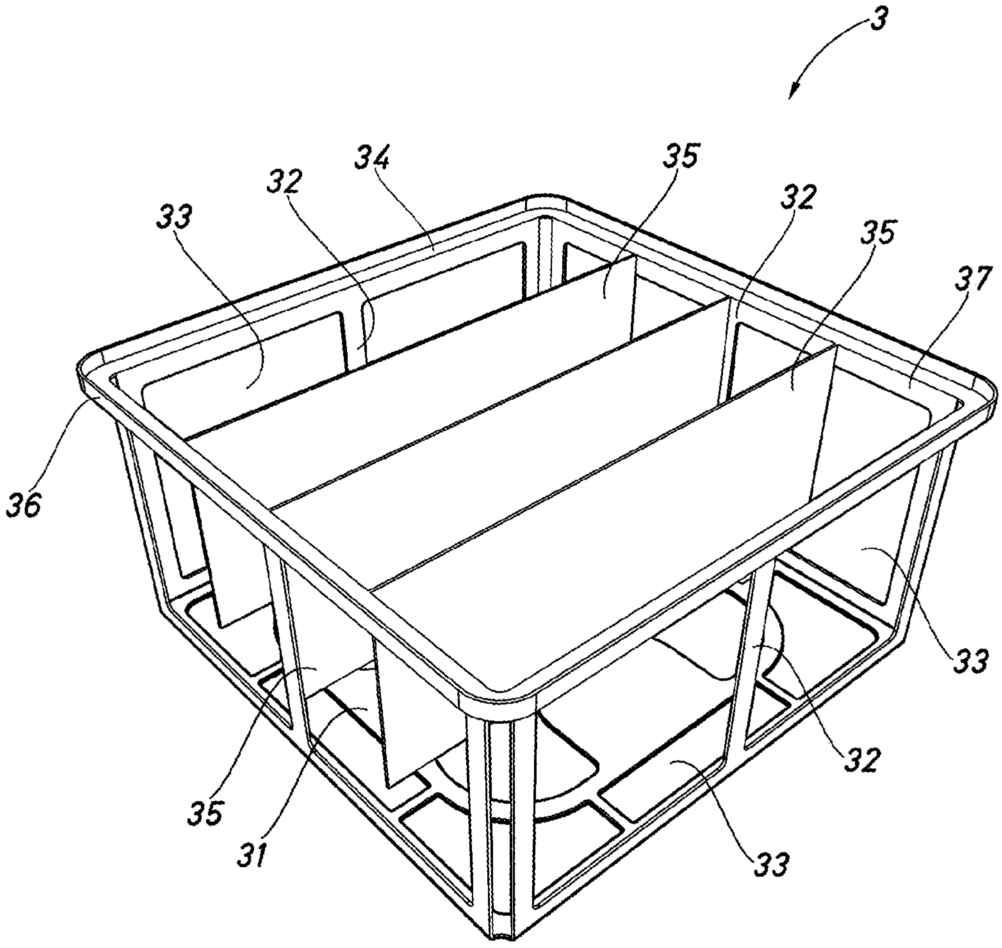
FIG. 2 is a perspective view of a preferred embodiment of the empty device with no cover.

FIG. 2 is a perspective view of a preferred embodiment of the device 3 with no cover. Said device comprises a substantially rectangular prism-shaped structure open at the upper face 37 and arranged to allow the syringe nests to be inserted therethrough. The inside of said structure communicates with the outside through openings 33 made in the lateral surfaces 32 and base 31 thereof, such that when introduced into the autoclave, steam can access the syringe nests arranged inside said structure (visible in FIGS. 4 and 5). Structures with other geometric shapes such as regular prisms, trapezoidal prisms or curved geometries are equally valid.

Figure 4:
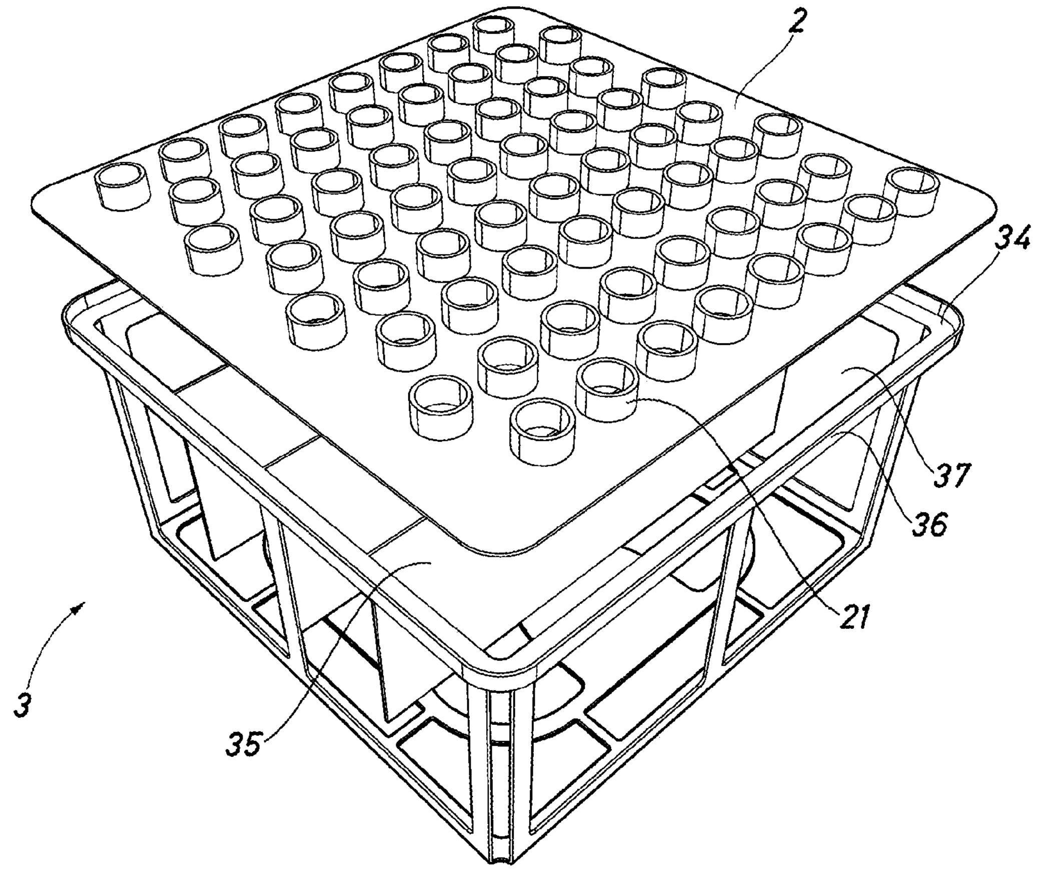
FIG. 4 is an exploded view of the embodiment of the device shown in FIG. 2, with a syringe nest and no cover.
Figure 8:
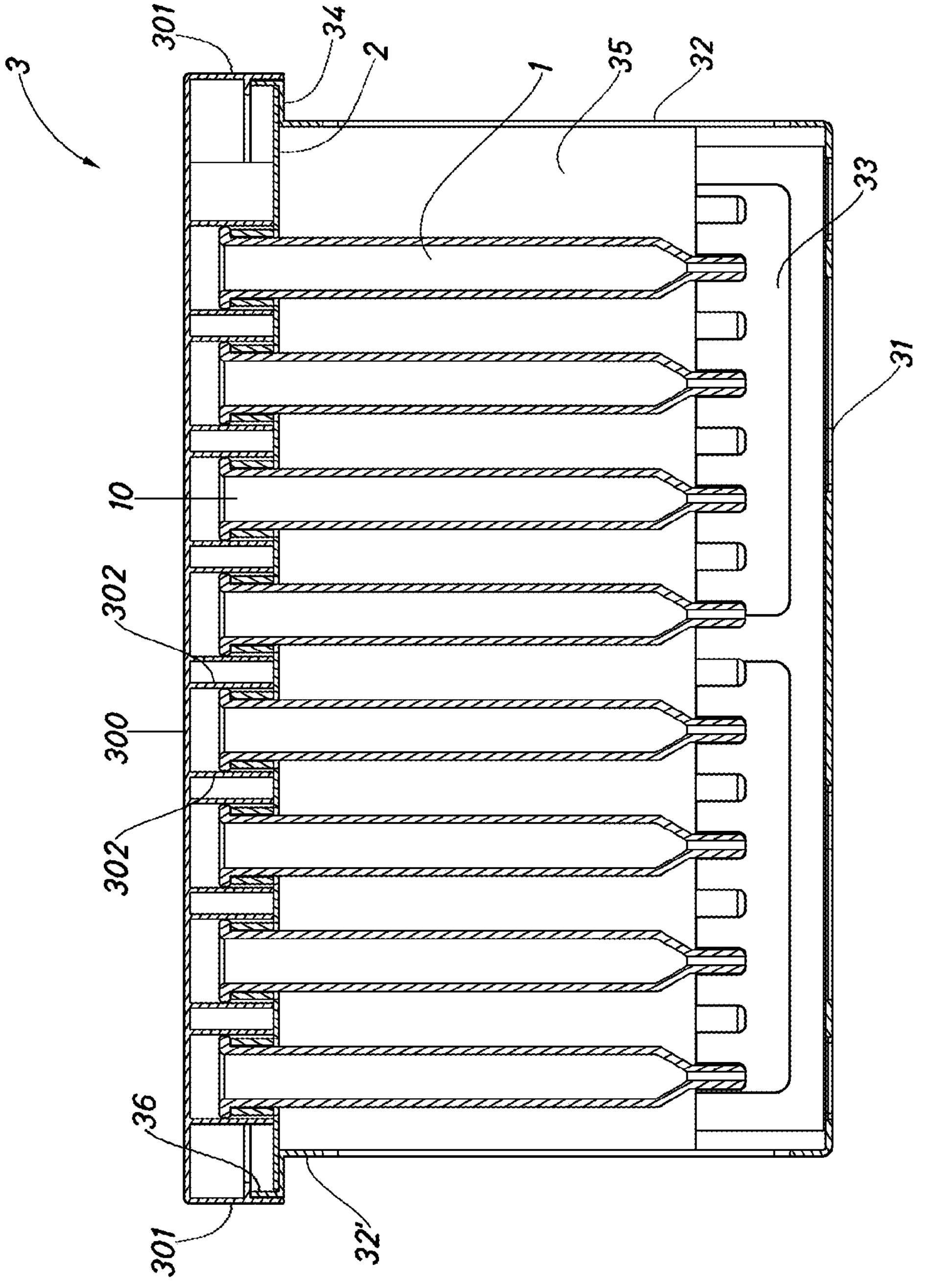
FIG. 8 is a view in cross section through the cutting plane BB' in FIG. 6.

Moreover, FIG. 2 shows that the device 3 comprises an inner edge 34 arranged to contact a peripheral portion of the syringe nest (as can be seen in the exploded view in FIG. 4 and in the view in cross section in FIG. 8, among others). Furthermore, the device 3 comprises support surfaces 35 between the lateral surfaces 32 thereof, said support surfaces 35 being arranged in turn to contact the syringe nests so that said syringe nests distribute the load of the syringes over various contact areas. In the present embodiment, said support surfaces 35 are three flat surfaces parallel to one another, which occupy a vertical space stretching from the base 31 to the inner edge 34. However, a different number, distribution and morphology of the support surfaces is equally valid, such as said surfaces being distributed in a Cartesian grid for example contained substantially in a horizontal plane parallel to the base 31 of the device 3.

In addition, the device 3 shown comprises a vertical surface 36 arranged on the perimeter area of the open upper face 37. This vertical surface 36 facilitates adjustment between the device 33 and the cover 300 thereof (not shown in the present figure). Said arrangement can be clearly seen in FIGS. 8 and 9.

Figure 3:
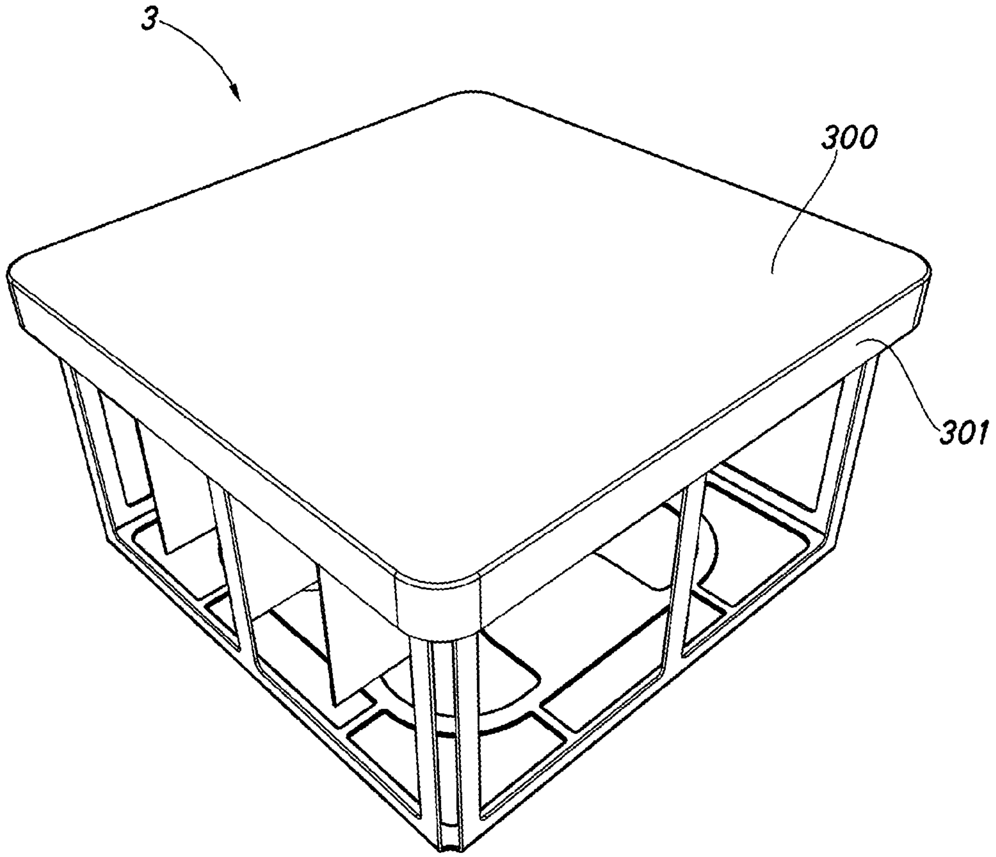
FIG. 3 is a perspective view of the embodiment of the device shown in FIG. 2, empty and with a cover.

FIG. 3 is a perspective view of the device 3 of FIG. 2 with a cover 300. As can be seen in the figure, said cover 300 has a skirt 301 which covers the vertical surface 36 arranged on the perimeter area of the open upper face 37 of the device 3, said vertical surface being hidden behind said skirt.

FIG. 4 is an exploded perspective view of the embodiment of the device 3 shown in FIG. 2 which contains a syringe nest 2. As can be seen in the figure, the syringe nest 2 may be introduced through the open upper face 37 of the device so that a peripheral portion thereof comes into direct contact with the inner edge 34 of the device 3. This contact area, together with the upper ends of the support surfaces 35, transfers the load from the syringe nest 2 to the device 3, thus reducing deformations of the nest 2. This is particularly advantageous during the sterilisation step, as many of the known commercially available nests 2 suffer deformations under load at high temperatures. Moreover, FIG. 4 shows that the nest 2 comprises hollow cylindrical extrusions 21 arranged to accommodate the syringes that are to be dosed.

Figure 5:
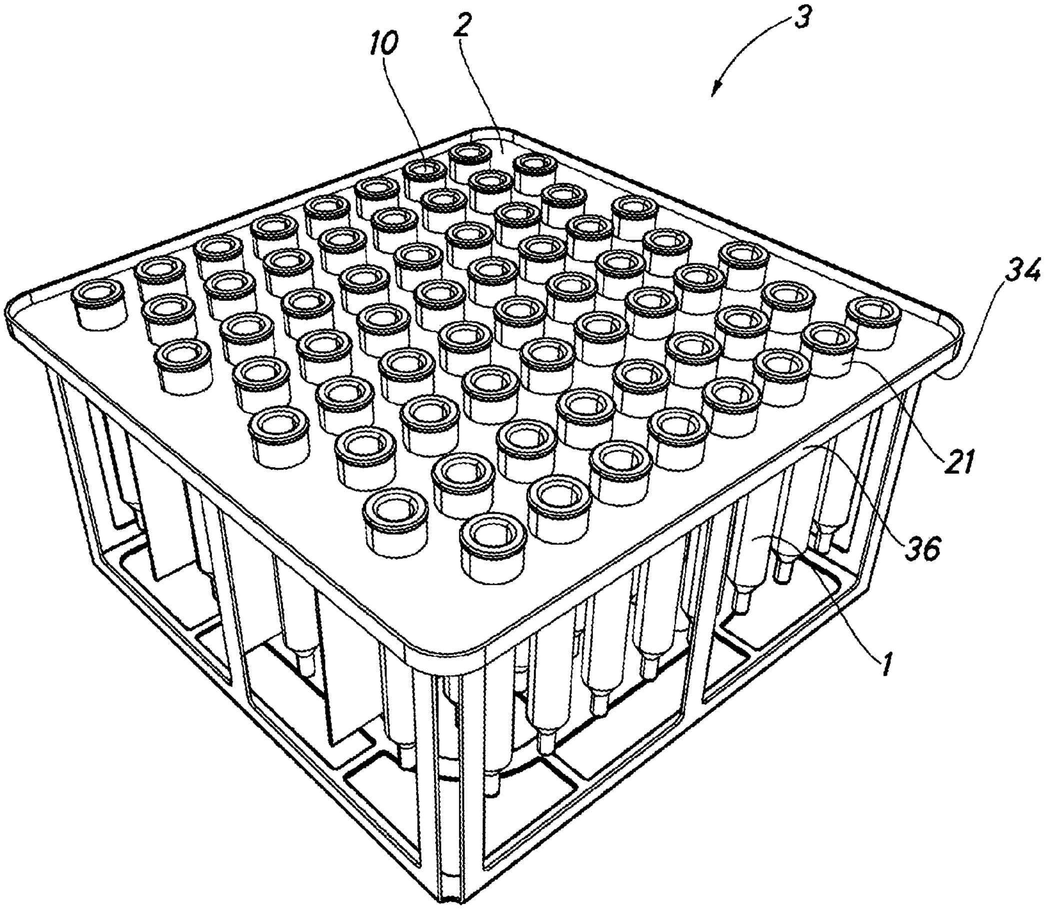
FIG. 5 is a perspective view of the embodiment of the device shown in FIG. 4, with the syringe nest inside.

FIG. 5 is a perspective view of the embodiment of the device and syringe nest 2 shown in FIG. 4, with the nest 2 inside the device 3. In the same way as shown in FIG. 4, the peripheral portion of the syringe nest 2 is in direct contact with the inner edge 34 of the device 3. The syringe nest 2 ensures that there is a distance between the open ends 10 of the syringes and the vertical surface 36, since the height of the hollow cylindrical extrusions 21 is preferably greater than said vertical surface 36. Moreover, the syringe nest 2 also provides horizontal distancing between the open ends 10, allowing the cover of the device to comprise protrusions which project towards the inside of the device and encircle the outside of said syringe cylinders, as can be clearly seen in FIGS. 8 and 9. If said distancing between the open ends 10 of the syringes did not exist, said protrusions projecting towards the inside of the device could encircle the inside of said open ends 10 of the syringes.

Figure 6:
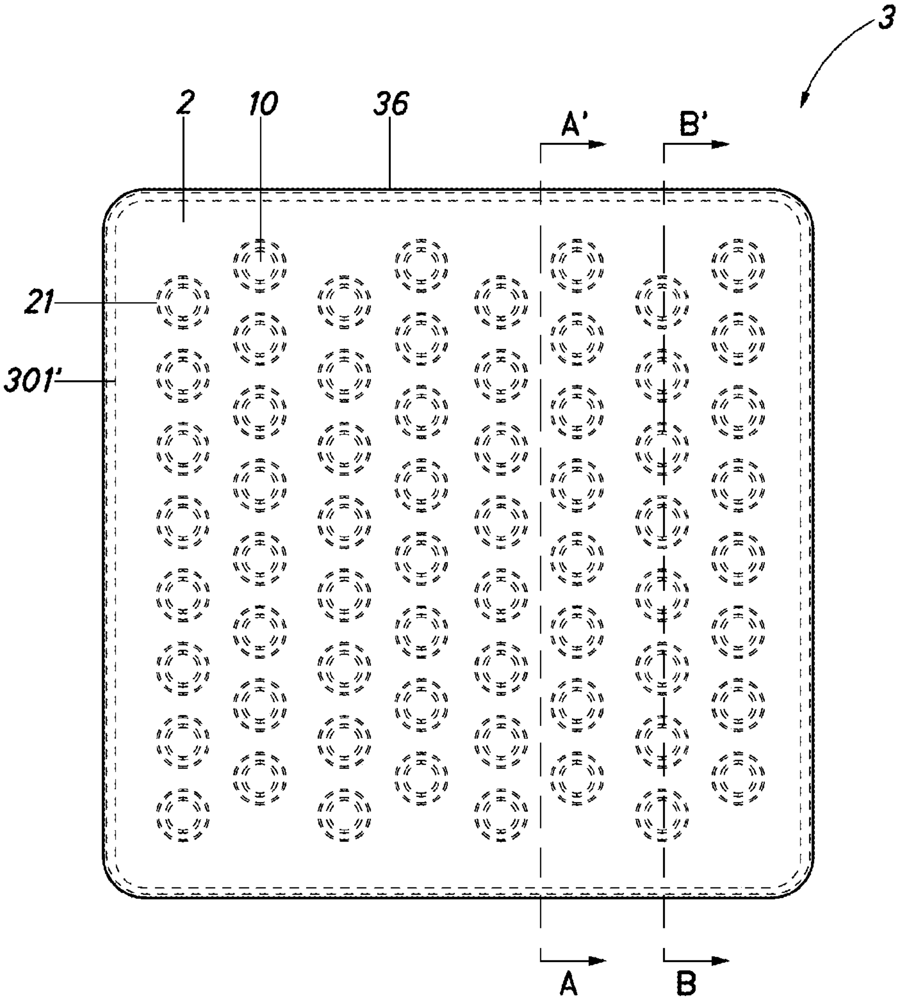
FIG. 6 is a plan view of the embodiment shown in FIG. 5, with the addition of a preferred embodiment of a cover.

FIG. 6 is a plan view according to FIG. 5 with the addition of a preferred embodiment of a cover, in which the above-mentioned horizontal distancing can clearly be seen. FIG. 6 shows the edges hidden directly behind the cover as dotted lines.

Figure 7:
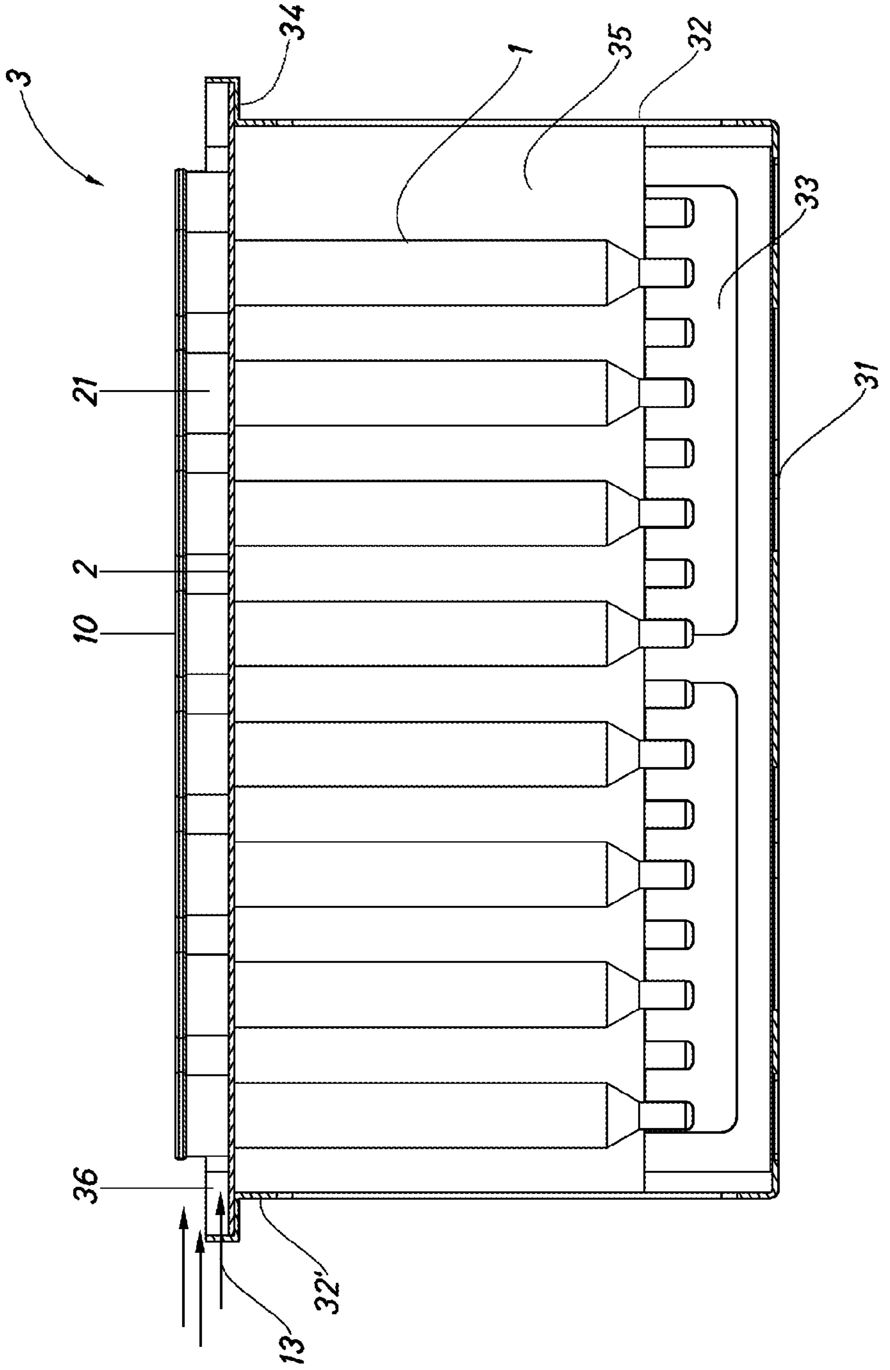
FIG. 7 is a view in cross section through the cutting plane AA' in FIG. 6 with no cover.

FIG. 7 is a view in cross section along the plane AA' shown in FIG. 6. In this figure, for clarity, the cover has not been shown. As well as the elements shown in FIG. 6, FIG. 7 also shows diagrammatically the direction and orientation of the horizontal laminar flow 13 in relation to the device 3. The arrangement shown of the unit made up of the syringes 1, the syringe nest 2 and the device 3 in relation to the horizontal laminar flow 13 is similar to that in the dosing step 12 (shown in FIG. 1). In FIG. 7, it can clearly be seen that the vertical surface 36 on which the horizontal laminar flow 13 is first incident is substantially lower in height than the hollow cylindrical extrusions 21, leaving a space free from obstructions between the vertical surface 36 and the open ends 10 of the syringes, so that the horizontal laminar flow 13 is not impeded by the device 3. This is particularly advantageous when the open ends 10 of the syringes are subjected to a horizontal laminar flow 13, as it allows the flow to maintain a laminar flow state when said flow passes over the vertical surface 36, significantly reducing the presence of turbulence in the vicinity of the open ends 10 of the syringes.

FIG. 8 is a view in cross section through the plane BB'. The cover 300 shown comprises a peripheral skirt 301 which surrounds the vertical surface 36 and, in this case, also contacts said vertical surface by means of a peripheral protrusion 301'. Accordingly, when the cover 300 is arranged on the device 3, access of a generic suspended particulate to the open end 10 of the syringes 1 arranged in the syringe nest 2 will be very much more difficult.

In addition, the cover 300 may also comprise protrusions 302 which project towards the inside of the device 3, encircling the perimeter of the open end 10 of the syringes and creating labyrinthine communication between the outside and the inside of the syringes 1.

Accordingly, when the cover 300 is positioned on the device 3, a suspended particulate outside the device 3 will be prevented from accessing the inside of the syringes 1.

Figure 9:
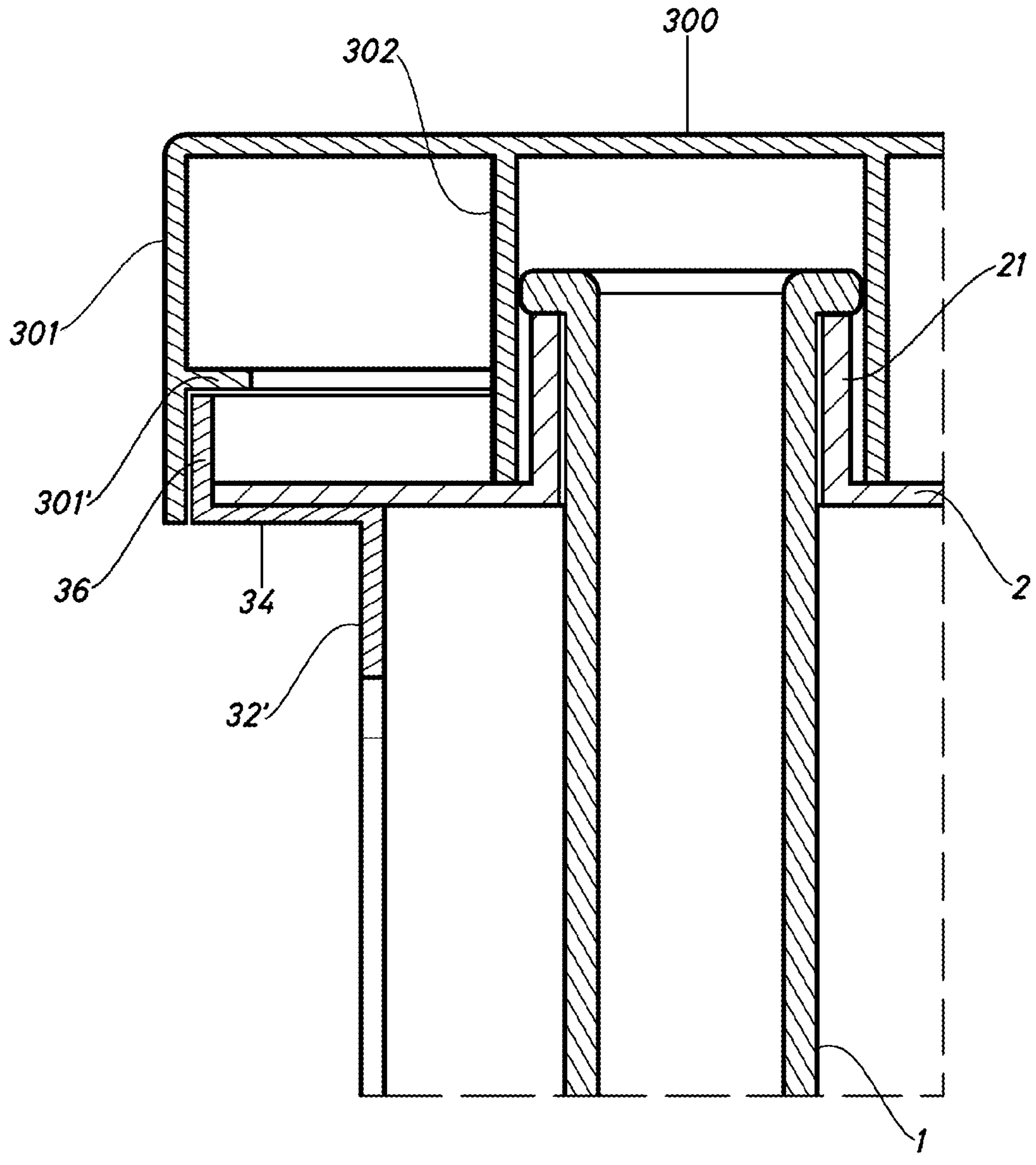
FIG. 9 is a detailed view of the relative arrangement between the device and a preferred embodiment of the cover.

FIG. 9 is a detailed view of the cross section shown in FIG. 8. In this figure, the points of contact between the different components can be clearly seen. Accordingly, it shows that the syringe nest 2 rests on the inner peripheral edge 34 of the device, and also shows the contact between the vertical surface 36 and the peripheral protrusion 301' of the skirt 301 of the cover 300. In addition, said figure shows how the protrusions 302 of the cover 300 encircle the open end of the syringe 1, and the arrangement of said syringe 1 on the hollow cylindrical extrusions 21.

Although the invention has been described with respect to a preferred embodiment, this should not be deemed to limit the invention, and it is possible to change structural or other details which may be obvious to a person skilled in the art after interpreting the subject matter disclosed in the present description, claims and drawings. In particular, in principle and unless explicitly stated, all the characteristics of the different embodiments and alternatives shown and/or suggested may be combined. Therefore, the protection of the present invention includes any variant or equivalent that could be considered covered by the widest interpretation of the following claims.

What is claimed is:

1. A method for dosing sterile syringes with medicinal products, comprising:

a) arranging a group of syringes in a syringe nest and the syringe nest in turn in a device;

b) sterilizing the syringes thus arranged, the sterilization being performed by a thermal process;

c) loading the devices with the sterile syringes in a dispensing system in order to dose the syringes;

d) uncovering, dosing and covering the syringes using a dosing system in the presence of a laminar flow;

wherein the device comprises:

a substantially prism-shaped structure in which at least an upper face is an open face which defines a perimeter area relative to the open face, the perimeter area having a vertical peripheral surface, the structure also comprising lateral surfaces with upper ends close to the open upper face and lower ends close to a base, the structure being arranged so as to allow the syringe nests to be inserted through at least said open upper face; and a cover, which, in the closed position, rests on the perimeter area of the open upper face of the device, the cover being arranged so as to cover the syringes, and wherein the device is configured to sterilize the nests and wherein the cover protects the inside of the syringes from suspended particulates by acting as a physical barrier.

2. The method according to claim 1, wherein sterilization is carried out in an autoclave with steam.

3. The method according to claim 2, wherein the cooling step is carried out in a sterile area of the autoclave.

4. The method according to claim 1, wherein the syringes are uncovered by removing the cover from the device.

5. The method according to claim 1, wherein the uncovering, dosing and covering are carried out in a dosing area which is in the presence of a laminar flow, wherein the laminar flow is a horizontal laminar flow, the devices being arranged in such a way that the base of the device is parallel to the horizontal laminar flow, so that a longitudinal axis of the syringes is substantially vertical and an open end thereof is facing upwards.

6. A device for receiving syringe nests, wherein the device is configured to carry out the method for dosing the sterile syringes according to claim 1.

7. The device according to claim 6, further comprising an inner edge on the perimeter area of the open upper face on which a peripheral portion of the syringe nest rests and support surfaces arranged between the lateral surfaces, so that the inner edge and the support surfaces distribute the load applied by the syringes to the device, thus reducing the stresses to which the syringe nest is subjected.

8. The device according to claim 6, wherein the cover of the device comprises protrusions which project towards the inside of the device, encircling open ends of the syringes.

9. The device according to claim 6, wherein the cover of the device comprises a skirt arranged around the perimeter thereof, encircling the device and contacting the vertical peripheral surface of the device by means of a peripheral protrusion.

10. The device according to claim 6, wherein the cover of the device comprises a fastener to act on the device.

11. The device according to claim 10, wherein the fastener is a dimensional interference fastener.

12. The device according to claim 10, wherein the structure of the device comprises a receptacle for receiving the fastener of the cover.

* * * * *